(12) United States Patent
Bertsch et al.

(10) Patent No.: US 10,368,887 B2
(45) Date of Patent: Aug. 6, 2019

(54) SURGICAL CLAMP INSERT WITH DIRECTION INDICATOR

(71) Applicant: Vitalitec International, Inc., Plymouth, MA (US)

(72) Inventors: Karrie Bertsch, Los Gatos, CA (US); Wayne R. Knupp, Jr., Kingston, MA (US); Ellen J. Knupp, Duxbury, MA (US)

(73) Assignee: Vitalitec International Inc., Plymouth, MA (US)

( * ) Notice: Subject to any disclaimer, the term of this patent is extended or adjusted under 35 U.S.C. 154(b) by 0 days.

(21) Appl. No.: 14/826,237

(22) Filed: Aug. 14, 2015

(65) Prior Publication Data

US 2016/0045213 A1 Feb. 18, 2016

Related U.S. Application Data

(60) Provisional application No. 62/037,786, filed on Aug. 15, 2014.

(51) Int. Cl.
*A61B 17/29* (2006.01)
*A61B 17/28* (2006.01)
*A61B 90/00* (2016.01)

(52) U.S. Cl.
CPC .. *A61B 17/2812* (2013.01); *A61B 2017/2808* (2013.01); *A61B 2017/2825* (2013.01); *A61B 2090/0808* (2016.02)

(58) Field of Classification Search
CPC ........ A61B 17/2816; A61B 17/320092; A61B 18/1442; A61B 2018/1455
See application file for complete search history.

(56) References Cited

U.S. PATENT DOCUMENTS

| | | | |
|---|---|---|---|
| 6,293,594 B1 | 9/2001 | Safarevich et al. | |
| 2006/0079874 A1* | 4/2006 | Faller | A61B 17/320092 606/40 |
| 2006/0195081 A1* | 8/2006 | Landis | A61B 17/2812 606/41 |

FOREIGN PATENT DOCUMENTS

| | | |
|---|---|---|
| CN | 202362033 | 8/2012 |
| JP | 2012122659 | 6/2012 |

OTHER PUBLICATIONS

International Application No. PCT/US15/45188 search report dated Oct. 16, 2015.

\* cited by examiner

*Primary Examiner* — Julie A Szpira
(74) *Attorney, Agent, or Firm* — Bachman & LaPointe, PC

(57) ABSTRACT

A pad configured to attach to a jaw of a surgical clamp includes an elongate body configured to extend over a surface of a jaw of a surgical clamp; and a flexible elongate attachment member connected to said body and configured for slidable insertion in a loading direction into an elongate cavity extending longitudinally through said jaw, wherein the elongate body has a first end and a second end, wherein the first end is configured to be inserted first into the cavity, and further comprising a direction indicator to identify which end is first inserted into said cavity. A surgical clamp utilizing the pad is also disclosed.

6 Claims, 5 Drawing Sheets

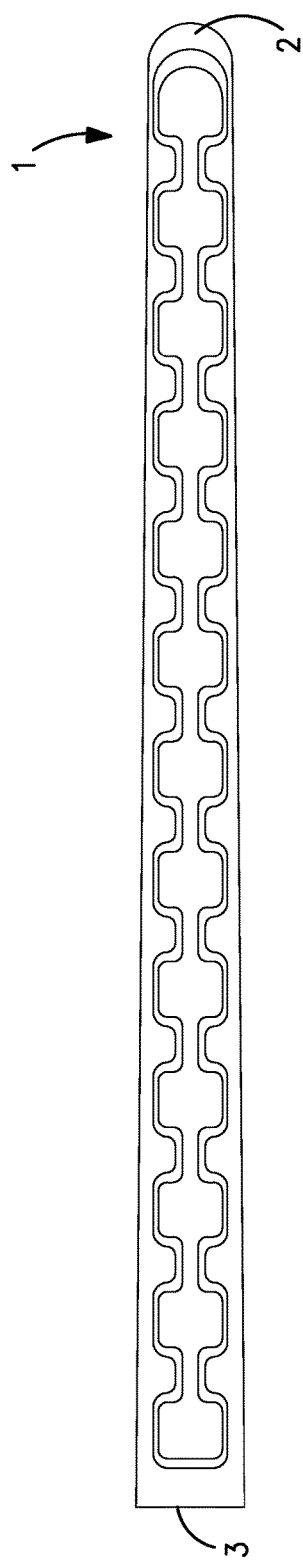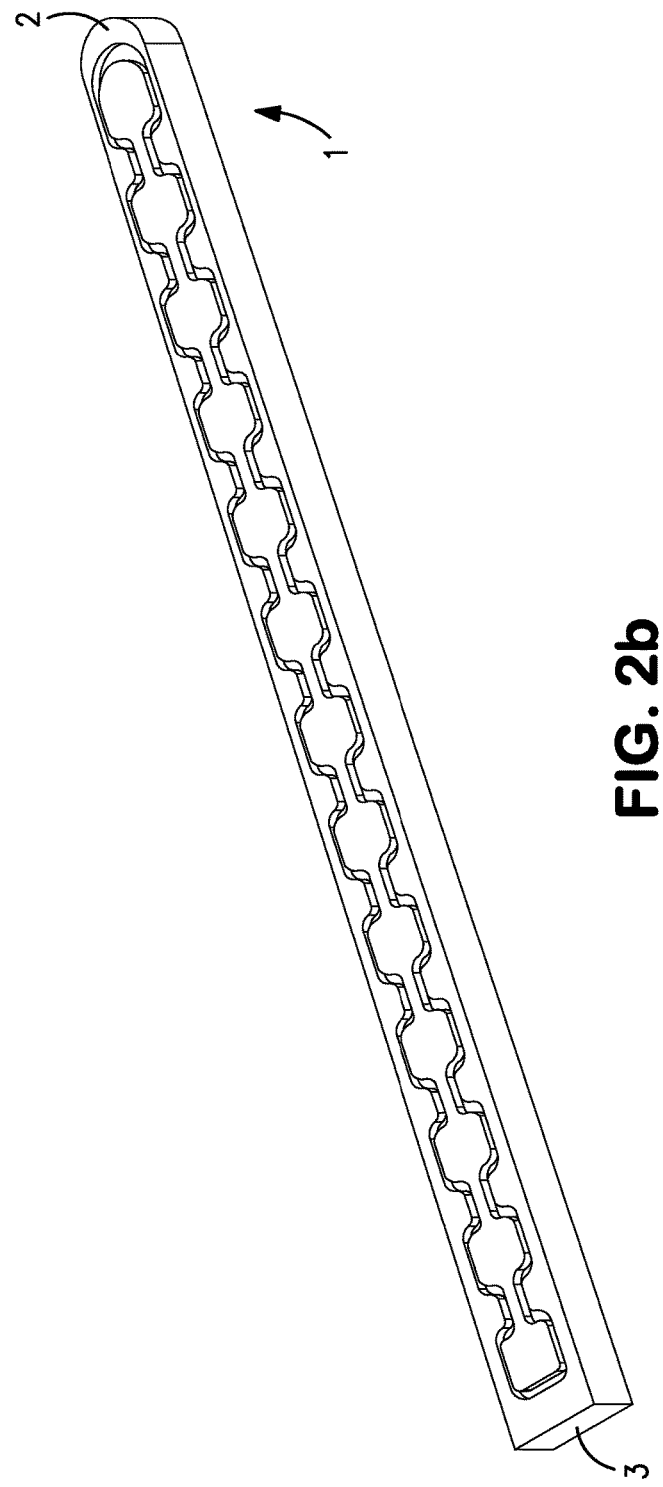

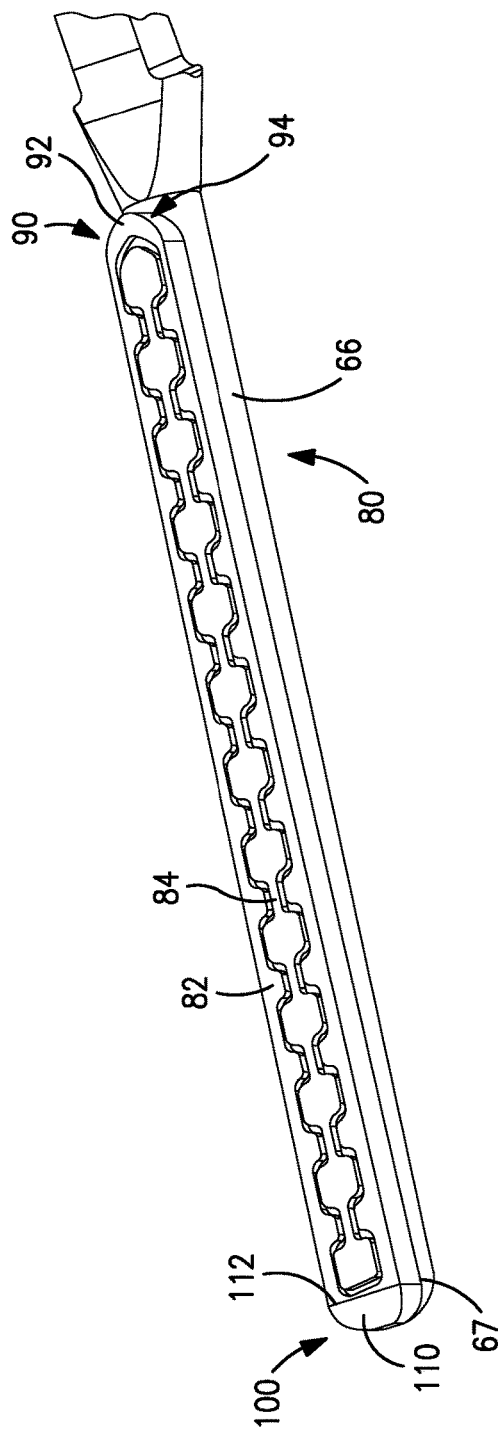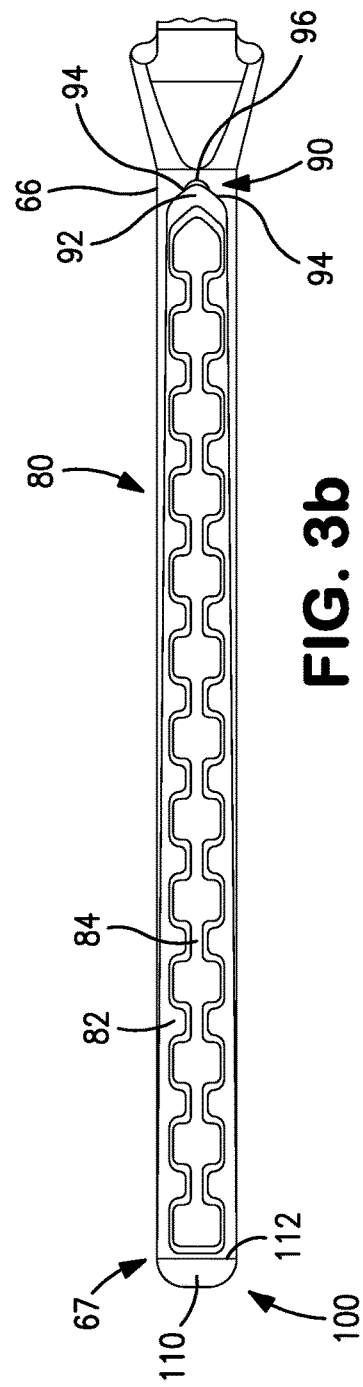
FIG. 3a
FIG. 3b

SURGICAL CLAMP INSERT WITH DIRECTION INDICATOR

BACKGROUND OF THE INVENTION

The invention relates to surgical clamps and, more particularly, to an insert for a surgical clamp.

Surgical clamps exist in many sizes with many different types of clamp shapes (e.g., curved jaws, straight jaws, etc.). In addition, many different types of jaw surfaces exist, as adapted to the specific function performed by the clamp. When a different function is to be performed, one must either use a different clamp, or in some circumstances replaceable pads may be added to the jaws.

Many existing surgical clamps have jaws with hard clamping surfaces. Some replaceable pads for these clamps are designed to fit over the jaws to provide a softer or otherwise different clamping surface. However, these pads are often bulky, reducing the sleekness of the clamp and jaws. In addition, these pads are typically designed to fit over only straight jaws and are generally straight themselves. There is a need for other shapes such as curved or S-shaped.

Other existing surgical clamps have curved, replaceable pads that are sleek, but these sleek pads are not soft and may be inappropriate for many applications.

Still other existing surgical clamps have soft pads but these pads are not replaceable. This makes the pads harder to clean. Autoclaving may cause soft or delicate pads to deteriorate or wear out more quickly; with the result that the pad surfaces may become less soft or less delicate. As an alternative, the pad surfaces may be constructed to be less soft or less delicate in order to have a longer lifetime.

Some surgical clamps (e.g., U.S. Pat. No. 3,503,398) have replaceable pads that are soft, but have other concerns. The pads are installed from the distal end, and may slip off from that direction. Decreasing the possibility of the pads slipping off may increase the effort necessary to install the pads. In addition, the portion of the pad that attaches to the clamp may not be flexible.

Finally, some existing surgical clamps have replaceable pads that are not tightly secured to the jaws. With such clamps, the pads may move laterally after the vessel or tissue has been clamped. This lateral movement makes for an insecure clamp subject to wobbling, that may shear or tear the vessel or tissue being clamped. A solution to many of these issues is addressed in U.S. Pat. No. 6,228,104 to Fogarty et al. and related patents, all assigned to the assignee of the present application.

In the above disclosures, situations arise where it is sometimes not as simple as desired to install a new pad or insert a clamp with desired capability. Further, there are additional functions which could be provided and/or enhanced with configuration of the insert. The present disclosure addresses these needs.

SUMMARY OF THE INVENTION

In accordance with the invention, the foregoing issues have been addressed. According to the invention, a pad or insert for a surgical clamp is provided which has a direction indicator to readily indicate to a user which end is first inserted into the channel of the surgical clamp. Further, since the configuration of the pad according to the present invention allows for a front or distal loading insert, the distal end of the insert can be provided with structure to provide enhanced or additional functions, such as, preferably, rounded edges which can provide additional capability in dissection and increased visualization, for example.

According to the invention, a pad is provided which is configured to attach to a jaw of a surgical clamp, and which comprises an elongate body configured to extend over a surface of a jaw of a surgical clamp; and a flexible elongate attachment member connected to said body and configured for slidable insertion in a loading direction into an elongate cavity extending longitudinally through said jaw, wherein the elongate body has a first end and a second end, wherein the first end is configured to be inserted first into the cavity, and further comprising a direction indicator at one of the first and second ends to identify which end is first inserted into said cavity.

Further according to the invention, a surgical clamp is provided, which comprises a pair of elongate jaws connected together for movement toward each other, at least one of said pair of jaws, and having a distal end and a surface in opposition to the other of said jaws; and an elongate cavity adapted for slidably receiving a clamp pad, the cavity extending longitudinally within said at least one jaw, wherein and said clamp pad comprises an elongate body configured to extend over a surface of said at least one jaw, and a flexible elongate attachment member connected to said body and configured for slidable insertion in a loading direction into the cavity of said at least one jaw, wherein the elongate body has a first end and a second end, wherein the first end is configured to be inserted first into said cavity, and further comprising a direction indicator at one of the first and second ends to identify which end is first inserted into said cavity.

Other objects and advantages of the present invention will be discussed further herein.

BRIEF DESCRIPTION OF THE DRAWINGS

A detailed description of preferred embodiments of the invention follows, with reference to the attached drawings, wherein:

FIGS. 2a and 2b show a prior art configuration of a pad for such a surgical clamp;

FIGS. 3a and 3b show a pad in accordance with the present invention;

DETAILED DESCRIPTION

Figure 1:
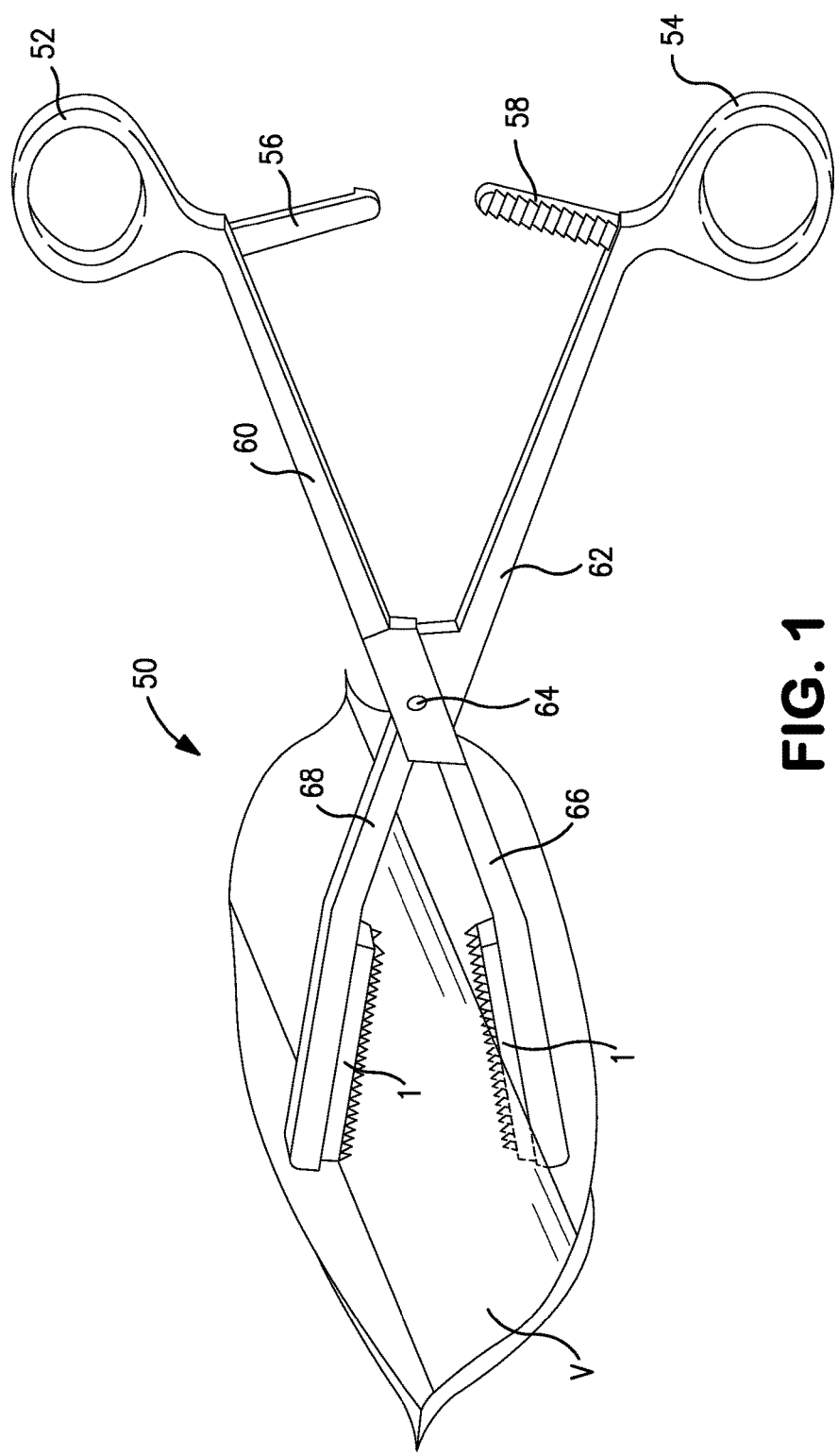
FIG. 1 shows a surgical clamp with pads or inserts.

FIG. 1 shows an exemplary surgical clamp 50 having jaws 66, 68 each including a pad 1. The clamp 50 is shown in the process of clamping a vessel V. It may also be used to clamp organs or other bodily tissue.

The clamp 50 can include finger and thumb rings 52, 54 for operating the clamp. A pawl 56 and ratchet teeth 58 can be provided to lock the clamp 50 when it is applied to vessel V. Handles 60, 62 are pivotally connected by pin 64. Jaws 66 and 68 apply a clamping force to vessel V, as cushioned by pads 80.

Jaws 66, 68 can have longitudinal channels which run at least the length of the jaws which are to be cushioned by pad 80. Pad 1 has an engaging structure which can be inserted into the channel of jaws 66, 68 to hold the pads securely in place for use in a surgical procedure while allowing the pad to be removed for changing the function of the clamp and/or sterilizing the clamp while disposing of a used pad.

FIGS. 2a and 2b show pads 1 which are known in the art, and which have a rounded end 2 and a squared off end 3 as shown. When pad 1 is to be inserted into the channel of jaws 66, 68, it is not immediately intuitive which end of the pad is first to be inserted. Further, inserting the wrong end first can result in an unstable clamp assembly, causing difficulty and potential delay during the surgical procedure.

Turning to FIGS. 3a and 3b, a pad 80 according to the invention is further illustrated, in this instance installed to a jaw 66 of a surgical instrument. As shown, pad 80 as illustrated is configured as a front loading clamp. This means that the pad is inserted into the distal end 67 of the jaw 66 of the clamp. The structure for engaging pad 80 with jaw 66 is further described below with reference also to FIG. 5.

Pad 80 has a cushion surface member 82 which is configured to provide the desired surface 84 for the surgical procedure being undertaken. Pad 80 also has an attachment member 86 (FIG. 5), preferably downwardly depending from surface member 82. Attachment member 86 preferably has a shape and size closely matching the shape and size of the channel 69 of the jaws so that attachment member 86 can be inserted into channel 69 to secure the pad relative to the jaw. Preferred materials and configurations of the attachment member and cushion surface member are discussed in the aforesaid U.S. Pat. No. 6,228,104, which is incorporated herein, in its entirety, by reference.

Figure 5:
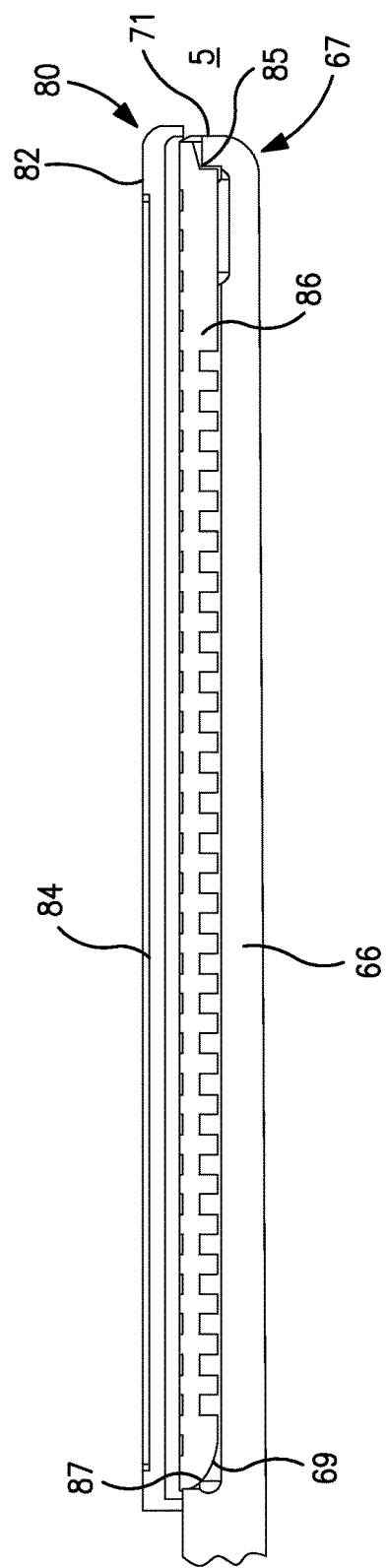
FIG. 5 is a cross sectional view of a pad according to the invention mounted in a jaw of a surgical instrument.

Still referring to FIG. 5, the attachment member 86 of pad 80 typically has a squared structure 85 which, as shown, is desired to interact with an upward projection 71 of jaw member 66. This engagement of features serves to hold pad 80 within jaw 66, against inadvertent sliding of pad 80 out of jaw 66. As also will be evident from a consideration of FIG. 5, the other end of attachment member 86 has a gradually curved surface 87. This gradually curved surface helps to provide a smooth entry of pad 80 into channel 69. It should also be appreciated, however, that in the event pad 80 is not oriented correctly for introduction into channel 69, the squared end 85 will make such insertion much more difficult, and the rounded edge 87 would serve to facilitate unintended or undesired removal of pad 80 out of channel 69.

In order to facilitate rapid recognition of the proper insertion orientation of the pad, pad 80 according to the invention has one end 90 (FIGS. 3a, 3b) with a direction indicator structure 92. In the embodiment illustrated, structure 92 is provided in the form of slanted or angled end surfaces 94 which terminate in and define an end point 96 which is oriented in the direction of insertion. Thus, a person looking to install pad 80 into a jaw would intuitively know to start with the pointing end 90 entering the channel 69 first, and then continue with insertion into the channel in the same direction in which end point 96 indicates, until the attachment member 86 is fully engaged in channel 69, preferably with structure 85 of pad 80 securely seated against structure 71 of jaw 66.

It should be appreciated that the direction indicator of the present invention is shown in FIGS. 3a and 3b in the form of end surfaces defining a point or arrow, but numerous other configurations could be provided which could also convey the direction of orientation of pad 80 for proper insertion. Of course, the illustrated embodiment is considered to be particularly advantageous as it can be incorporated without major change in the overall shape or structure of existing pads, thereby maintaining functionality with existing clamps.

Still referring to FIGS. 3a and 3b, the other end 100 of pad 80 according to the invention can be provided with additional structure to enhance functionality of the device. This is particularly true with a pad 80 and jaws 66, 68 configuration wherein the pad is front inserted, since such a configuration leaves end 100 as the distal facing end, where additional functionality is possible.

Figure 4:
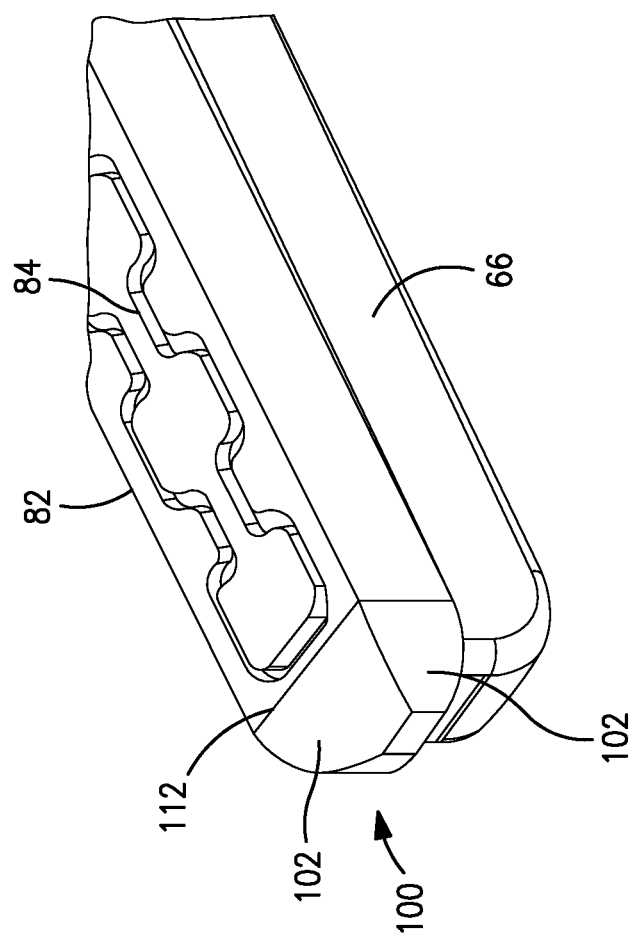
FIG. 4 shows an end of a pad configured to provide additional function in dissection.

According to the embodiment shown in FIGS. 3a and 3b, and further illustrated in FIG. 4, end 100 can have a series of rounded edges 102 which can help in using the distal end of the clamp for example in a dissection procedure.

End 100 with rounded edges 102 is decidedly more pointed and wedge-shaped than the flat blunt end of known pads (See end 3, FIGS. 2a and 2b). Further, the rounded edges increase visibility at the distal edge of the pad, which is a critical point for having maximum visibility for the surgeon. During a dissection process, the distal jaw end can frequently be used as a "wedge", wherein the surgeon pushes the distal jaw end through tissue to separate it. When the end is more rounded, pointed or tapered, it can push more easily through tissue. In this regard, and as clearly shown in FIGS. 3a and 3b, when end 100 is also to have rounded edges to help define a dissection surface, the upper tapered surface 110 of end 100 is preferably defined and angled downwardly from surface 84 at a visible straight line 112. This visible straight line 112 helps to distinguish end 100 with rounded edges from end 90 with a direction indicator defined thereon.

It should also be appreciated that while the present invention is disclosed in terms of a front loading pad, that is, a pad which is inserted into the channel of a jaw through a distal end of the jaw, the pad configuration of the present invention is readily adaptable to rear loading jaws as well, wherein the pad is loaded into the channel of a jaw from a proximal surface of the jaw. In either configuration, end 90 of pad 80 is advantageously configured to indicate the proper direction of insertion. For rear-loading jaws, end 90 would have rounded surfaces on attachment member 86 to facilitate introduction into channel 69, while attachment member 86 at the other end of pad 80 would have a squared off structure designed for interaction with channel 69 to hold pad 80 within jaw 66 as desired. It should also be appreciated that in this configuration, end 90 of pad 80 also serves as the distal end of the clamp, and the pointed structure defining the arrow or other type of direction indicator on the pad can also serve to enhance visibility and use of the distal end of the clamp for dissection purposes as indicated above.

One or more embodiments of the present disclosure have been described. Nevertheless, it will be understood that various modifications may be made without departing from the spirit and scope of the disclosure. Accordingly, other embodiments are within the scope of the following claims.

What is claimed is:

1. A pad configured to attach to a jaw of a surgical clamp, comprising:
   an elongate body configured to extend over a surface of a jaw of a surgical clamp; and
   a flexible elongate attachment member connected to said body and configured for slidable insertion in a loading direction into an elongate cavity extending longitudinally through said jaw, wherein the elongate body has a first end and a second end, wherein the first end is configured to be inserted first into the cavity, and further comprising a direction indicator to identify which end is first inserted into said cavity, wherein said attachment member is configured to insert into an open distal end of said jaw into said elongate cavity, and wherein said direction indicator is on a proximal end of said elongate body, further comprising a cushioned surface member on the elongate body, wherein the direction indicator comprises angled edges defining a terminal point oriented in said loading direction, and wherein the cushioned surface member has a shape at a proximal end which is contoured to match the angled edges of the direction indicator.

2. The pad of claim 1, wherein the attachment member is configured for longitudinal sliding into said elongate cavity of said jaw, and wherein said direction indicator points in a direction of insert of said attachment member into said elongate cavity.

3. The pad of claim 2, wherein said distal end of said elongate body has rounded surfaces.

4. A surgical clamp, comprising:
a pair of elongate jaws connected together for movement toward each other, at least one of said pair of jaws having a distal end and a surface in opposition to the other of said jaws, and an elongate cavity adapted for slidably receiving a clamp pad, the cavity extending longitudinally within said at least one jaw;
wherein said clamp pad comprises an elongate body configured to extend over a surface of said at least one jaw, and a flexible elongate attachment member connected to said body and configured for slidable insertion in a loading direction into the cavity extending longitudinally through said jaw, wherein the elongate body has a first end and a second end, wherein the first end of the first and second ends is configured to be inserted first into said cavity, and further comprising a direction indicator to identify which end of the first and second ends is first inserted into said cavity, wherein said attachment member is configured to insert into an open distal end of said jaw into said elongate cavity, and wherein said direction indicator is on a proximal end of said elongate body, and further comprising a cushioned surface member on the elongate body, wherein the direction indicator comprises angled edges defining a terminal point oriented in said loading direction, and wherein the cushioned surface member has a shape at a proximal end which is contoured to match the angled edges of the direction indicator.

5. The surgical clamp of claim 4, wherein the attachment member is configured for longitudinal sliding into said elongate cavity of said jaw, and wherein said direction indicator points in a direction of insert of said attachment member into said elongate cavity.

6. The surgical clamp of claim 4, wherein said distal end of said elongate body has rounded surfaces.

* * * * *